United States Patent [19]

Goldstein

[11] Patent Number: 4,500,510
[45] Date of Patent: Feb. 19, 1985

[54] **DAMAGED FISH TISSUE TREATING METHOD AND COMPOSITION CONTAINING *ALOE VERA* EXTRACT**

[75] Inventor: Joel Goldstein, Ambler, Pa.

[73] Assignee: Aquarium Pharmaceuticals, Inc., Perkasie, Pa.

[21] Appl. No.: 501,990

[22] Filed: Jun. 7, 1983

Related U.S. Application Data

[63] Continuation-in-part of Ser. No. 426,351, Sep. 29, 1982, abandoned.

[51] Int. Cl.³ .................. A61K 31/79; A61K 35/78
[52] U.S. Cl. ................................ 424/80; 424/195.1
[58] Field of Search .................... 424/195, 80, 164

[56] References Cited

U.S. PATENT DOCUMENTS

| | | | |
|---|---|---|---|
| 229,874 | 7/1880 | Dengel | 424/195 |
| 254,448 | 3/1882 | Averhoff | 424/195 |
| 273,552 | 3/1883 | Larsen | 424/154 |
| 279,166 | 6/1883 | Huffman | 424/127 |
| 288,630 | 11/1883 | Green | 424/195 |
| 392,776 | 11/1888 | Bizzozero et al. | 424/195 |
| 1,167,230 | 1/1916 | Tambach | 424/195 |
| 2,963,400 | 12/1960 | Ross et al. | 424/114 |
| 3,878,197 | 4/1975 | Maret | 260/236.5 |
| 3,892,853 | 7/1975 | Cobble | 424/195 |
| 4,178,372 | 12/1979 | Coats | 424/195 |

OTHER PUBLICATIONS

Dr. Madis Laboratories, Inc., Water Soluble and Oil Soluble Lipoid Veragel, Review of Aloe Vera History, Pharmacognosy, Chemistry, Pharmacology and Application, ISBN:9-941350-00-2, 1982, Bulletin No. 3M82-1501.

Encyclopedia of Chemical Technology, vol. 21, 2nd Edition, pp. 427–440 (1970).

GAF Corporation Technical Bulletin No. 7543–113, PVP (Polyvinylpyrrolidone), (1964).

*Primary Examiner*—Albert T. Meyers
*Assistant Examiner*—John W. Rollins
*Attorney, Agent, or Firm*—Panitch Schwarze Jacobs & Nadel

[57] ABSTRACT

A composition comprising an extract of the *Aloe vera* Linne plant is used to promote healing of damaged fish tissue. It may be used with one or more agents for replacing the natural mucoprotein secretion which coats the skin and scales of fish. The composition may be added to either fresh water or salt water.

11 Claims, No Drawings

DAMAGED FISH TISSUE TREATING METHOD AND COMPOSITION CONTAINING *ALOE VERA* EXTRACT

CROSS REFERENCE TO RELATED APPLICATION

This application is a continuation-in-part of U.S. application Ser. No. 426,351, filed Sept. 29, 1982, entitled Fish Treating Composition Containing Aloe Vera Extract And Method For Treating Damaged Fish Tissue, now abandoned.

BACKGROUND OF INVENTION

The present invention is directed to a composition containing an extract of aloe vera which, when added to water containing fish, such as aquarium water, is useful in promoting the healing of injured or damaged fish tissue. The aloe vera extract is a leaf extract of the aloe vera plant.

Every fish has a natural mucoprotein or "slime" coating covering its skin and scales. The slime coating is the fish's first line of defense against infection. Recent literature indicates that the slime coating contains enzymes and antibodies to fight infection. The slime coating acts as a shield against disease causing organisms in the fish's external environment. It also acts as a barrier to prevent loss of internal electrolytes and body fluids. It is believed that when even a small portion of the slime coating is removed, the fish will bleed electrolytes from its body into the surrounding water.

Beneath the fish's mucoprotein coating are its scales which can extend to the outer skin surface from the underlying dermal connective tissue. Beneath the scales in a fish's skin is the epidermis, comprising several layers of cells. The fish epidermis is distinguished from mammalian epidermis in that mammals require hardened layers of skin to prevent dehydration, whereas in the aquatic environment, the fish has no need for such protection. Thus, unlike the case in mammals, mitosis is usually seen in the lower layer of the epidermal layer of a fish. Beneath the epidermis of a fish is the dermis comprising fibrous connective tissue interspersed with black pigment cells. The vascular dermal tissue contains a network of capillaries providing nutrient to the skin.

Because a fish is an aquatic animal, its skin differs from that of other animals, and notably mammals. Accordingly, there is no reason to believe that the skin treatment of one type of skin animal, for example, a mammal, would be effective to treat the skin of another type of animal, for example, a fish.

When a fish is netted, handled or even at times when placed in a stressful situation, such as low oxygen, high carbon dioxide or temperature fluctuations, the slime coating is disturbed, making the fish vulnerable to disease, such as bacterial, fungal and parasitic diseases. Particularly when fish are shipped in high concentrations in low volumes of water, they are subject to trauma such as being scraped, bitten and otherwise wounded. Moreover, ammonia, a waste product of fish's digestion and respiration, is released into the water containing fish. Ammonia is also released at high levels by dead fish and decaying food. At high ammonia levels, the fish are subject to ammonia burns which disturb the slime coating and adversely affect the fish.

This invention is based on the discovery that aloe vera extract promotes the healing of damaged fish tissue, and increases the effectiveness of compositions used to replace the fish's slime coating.

Although aloe vera has been known for centuries in the treatment of a wide range of human skin ailments, its use in treating damaged fish tissue is hitherto unknown. Further, compositions for replacing the slime coating of aquarium fish are known. These compositions generally contain colloids which replace a fish's natural mucous secretion. However, no prior art slime-replacing composition is known to contain aloe vera.

DEFINITIONS

As used herein, "Aloe Vera" is the plant Aloe vera Linne, sometimes referred to as *Aloe barbadensis* Miller, which is known to those skilled in the art to be the variety of the Aloe vera plant used in the cosmetic industry.

As used herein, "aloe vera extract" means either the liquid extract or gel obtained directly from the inner central zones of the leaves of the Aloe vera plant, or the gel reconstituted from powdered aloe vera extract.

As used herein, a fish's tissue is "damaged" when at least a portion of the slime coating is removed, for example, by scraping, bites from other fish or animals, netting, handling, wounds, ammonia burns, or as the result of bacterial, fungal or parasitic infection.

As used herein, the "fish" which may be treated effectively with the aloe vera extract are substantially any species or varieties of fish which are confined in a reasonable space, such as for breeding, holding, and shipping. Typically, fish treated in accordance with the present invention would be fish held in aquariums of various sizes. It is believed to be impractical to treat fish economically in accordance with the present invention when fish are contained in a large lake, river, or other such body of water. However, fish contained in breeding ponds are specifically included herein.

As used herein, "promote healing" means to heal more quickly and/or more completely. The term is based upon the observation that treatment in accordance with the present invention causes the healing of damaged tissue which did not appear to heal within a reasonable time by itself without the treatment in accordance with the present invention.

As used herein, a fish is "treated" according to the present invention when aloe vera extract is administered topically to the fish, as by adding the aloe vera extract to the water containing the fish.

SUMMARY OF THE INVENTION

A process for treating damaged tissue of fish is provided comprising topically administering to the fish an extract of the Aloe Vera plant in an amount effective to promote healing of the damaged tissue. An aqueous composition for treating damaged tissue of fish is provided containing as the active ingredient an extract of the Aloe Vera plant in an amount effective to promote healing of the damaged tissue.

DETAILED DESCRIPTION OF THE PREFERRED EMBODIMENTS

The essence of the present invention is the administration of a composition comprising aloe vera extract which, when administered to the damaged tissue of fish, preferably by being added to the fish-containing water in an effective amount to promote healing of the damaged tissue, is beneficial to the fish. The aloe vera extract may be and preferably is used with other ingredients to replace the slime coating of fish which is often removed when fish are injured.

Aloe vera extract in the form of a gel may be obtained directly from the thin-walled tubular cells in the inner central zone of the leaf (mucilaginous parenchyma) of the Aloe vera Linne plant. The raw gel should contain a small quantity of preservative if it is to be stored. Suitable preservatives include 0.15 percent methyl paraben and 0.30 percent imidazolidinyl urea. The gel may be dried, preferably lyophilized, and powdered. If desired, before use, the powdered aloe vera gel may be reconstituted in water, preferably with high speed mixing in warm water. Applicant has used successfully in his invention both liquid VERAGEL aloe vera gel, Product No. 1501, and powdered aloe vera extract, such as "VERAGEL 200," both available from Dr. Madis Laboratories, Inc., South Hackensack, N.J. The powdered VERAGEL 200 works well when reconstituted in 200 parts by weight of water. When the powdered VERAGEL 200 is reconstituted with 200 parts of warm water it has the same aloe vera concentration as the VERAGEL No. 1501. The VERAGEL products are described more specifically in Bulletin No. 3M82-1501 of Dr. Madis Laboratories, Inc., the disclosure of which is hereby incorporated herein by reference.

Only very small concentrations of aloe vera extract are necessary to stimulate and promote healing, as set forth in Examples 1 and 2 below. Generally, it is believed that adding aloe vera gel to water containing the fish in concentrations of about 0.00165 volume percent (about ⅛ teaspoon per 10 gallons) to about 0.026 volume percent (about two teaspoons per 10 gallons) of liquid aloe vera gel, based on the water containing the fish, is effective. Presently, about 0.0033 volume percent (about ¼ teaspoon per 10 gallons) is the preferred dosage of the liquid aloe vera gel. Likewise it is believed that adding to water containing the fish about 0.0012 g/l to about 0.013 g/l of powdered aloe vera extract, based on the water containing the fish, is effective. Presently, about 0.0066 g/l (about 0.25 grams per 10 gallons) is the preferred dosage if powdered aloe vera extract is added directly to the water containing the fish.

In addition to the administration of aloe vera extract itself, the present invention contemplates the inclusion of aloe vera extract in a composition which replaces a fish's slime coating.

The composition preferably contains polyvinylpyrrolidone ("PVP") and carboxymethyl cellulose ("CMC"), both of which act to replace the fish's natural mucoprotein slime coating secretion. PVP is readily available commercially in the United States in four viscosity grades having molecular weights of about 10,000, 40,000, 160,00 and 360,000. The PVP preferred for the present invention is the PVP having the molecular weight of about 40,000 (K-30 available from GAF Corporation). PVP having a higher molecular weight appears to have a gill clogging effect. PVP having an appreciably lower molecular weight would not seem to coat as well. However, it is believed that PVP having molecular weights over a wide range around 30,000 should be effective in replacing the slime coating. It is believed that an efective amount of PVP with a molecular weight of about 40,000 which would be effective to promote the replacement of the natural slime coating of fish would be about 1.3 to about 25 g/l of the composition.

The preferred CMC optionally used in the present invention is sodium carboxymethyl cellulose having a viscosity of 2,500 cps. As with the PVP, the CMC can be of several types and have a wide range of viscosities, so long as it aids in replacing the slime coating and does not adversely affect the fish, as by blocking the gill lamella. It is believed that an effective amount of sodium carboxymethyl cellulose with a viscosity of 2,500 cps to replace the slime coat would be up to about 7.5 g/l of the composition.

Also present in preferred embodiments of the composition are a dechlorinating agent, such as sodium thiosulfate or asorbic acid, in an amount effective to neutralize the free chlorine or organic chlorine compounds, such as chloramine, in the water. Sodium thiosulfate is presently preferred. To be effective, it is believed that the sodium thiosulfate should be present in an amount of about 12.5 to about 60 g/l of the composition.

The preferred embodiment of the composition also includes a chelating agent, such as ethylenediaminetetraacetic acid ("EDTA"). The chelating agent should be present in an amount sufficient to react with and bind potentially and actually toxic heavy metals in the water. Effective amounts of EDTA are believed to be up to about 2 g/l of the composition. This ingredient is also optional and not essential, unless at least potentially toxic levels of heavy metals are contemplated in the water.

A buffering agent, such as tris(hydroxymethyl)aminomethane, is also included in the preferred embodiment. The buffer should be present in an excess to maintain the pH of the composition above about 9.0 so that the sodium thiosulfate is stabilized. It is believed that an effective amount of tris(hydroxymethyl)aminomethane is about 0.3 to about 1 g/l of the composition.

A preservative should also be included so that the aloe vera extract retains its curative properties during storage. A suitable preservative is diazolidinyl urea. It is believed that an effective amount of preservative would be about 1.3 to about 4 g/l of the composition.

The most practical way of administering aloe vera extract to fish is by adding it directly or in a composition containing it either to fresh water or to salt water in aquariums. It may also be added very beneficially as a protective and healing agent to water contained in vessels or bags used to ship fish prior to or during the shipping process.

The present invention will now be described and explained further by reference to the following specific, illustrative, non-limiting examples. Examples 1-3 demonstrate the effectiveness of aloe vera extract in treating damaged fish tissue. Example 4 describes the preparation of an aloe vera composition containing slime-replacing compounds.

EXAMPLES 1

Liquid Aloe Vera Gel Composition Test on Fish

A goldfish was placed in a tank with 10 gallons of water after having some of its scales removed. Severe hemorrhaging was observed at the location of scale removal. Powdered aloe vera gel extract ("VERAGEL 200") was rehydrated in 200 parts by weight of water to form an aqueous solution of aloe vera extract. One-half teaspoon of the aqueous solution was added to the aquarium water on day 1. The tank water was changed on days 9, 18 and 28. After each water change, the aloe vera gel solution concentration was restored by the addition of one-half teaspoon to the tank water. On day 28, the damaged area remained visible, but rawness and bleeding had ceased. Tissue regeneration was noted and no signs of secondary infection were visible.

EXAMPLE 2

Powdered Aloe Vera Gel Composition Tested on Fish

In another tank containing 10 gallons of water, the procedure of Example 1 was carried out on another goldfish, substituting powdered aloe vera gel extract ("VERAGEL 200") for the aqueous solution of Example 1. As before, fish scales were removed. The powdered extract was administered after water changes on the following days:

| Day 1 | Day 9 | Day 18 | Day 28 |
| --- | --- | --- | --- |
| 1.0 g. | 0.25 g. | 0.25 g. | 0.2 g. |

On day 28 the fish had almost completely healed. No raw areas or signs of bleeding were visible. Rapid tissue regeneration was noted and only smooth tissue remained over the damaged area.

EXAMPLE 3

Control

A goldfish having some of its scales removed was contained in a separate tank. No aloe vera gel composition was added to the tank. Water was changed on days 9, 18 and 28. On day 28 the fish demonstrated continued severe raw tissue and blood spots. The tissues showed no signs of regeneration.

EXAMPLE 4

Preparation of Liquid Aloe Vera Gel Slime-Replacement Composition

A 40 liter batch of aqueous aloe vera gel composition containing slime-replacing compounds was prepared by mixing the following ingredients in the following proportions in accordance with the indicated procedure.

| Aloe vera gel ("VERAGEL 1501") | 4 liters |
| --- | --- |
| sodium thiosulfate | 1400 g |
| carboxymethyl cellulose | 100 g. |
| polyvinylpyrrolidone | 400 g. |
| ethylenediaminetetraacetic acid | 40 g. |
| tris(hydroxymethyl)aminomethane | 17 g. |
| diazolidinyl urea | 80 g. |
| deionized water | enough to dilute to a total volume of 40 liters |

About 10 liters of the water were added into a small mixing chamber of a high speed shear mixer and, with the mixer on, approximately half of the carboyxmethyl cellulose was dissolved in the water. When the mixture was smooth, the mixture was transferred into the mixing chamber of a medium speed mixer, such as a LIGHTN'N Mixer. The remaining carboxymethyl cellulose should be mixed with the water as indicated above in the small mixer and then added to the mixing chamber of the medium speed mixer.

The mixing chamber of the small mixer was filled with about 10 liters of water and the PVP was mixed with the water while the mixer ran at high speed. When this mixture was smooth, it was added, with mixing, to the carboxymethyl cellulose mixture in the medium speed mixer.

While the medium speed mixer was operating, the following ingredients were added to the mixing chamber: sodium thiosulfate, EDTA, buffer, preservative and aloe vera gel. While mixing continued, sufficient water was added to make a total volume of 40 liters. After mixing until all ingredients were well blended, the composition was put into several containers.

The composition of Example 4 is preferably added directly to aquarium fish water. Although lower dosages may be effective, the recommended dosage is one teaspoonful per ten gallons of aquarium water where the water contains free chlorine. When the water contains organic chlorine compounds, such as chloramine, the recommended dosage is two teaspoons per ten gallons of aquarium water. At this dosage, the diluted concentration, after being added to the fish containing water, is equivalent to about 0.013 volume percent for the composition and about 0.0013 volume percent for the aloe vera active ingredient.

Additional testing with the composition of Example 4 was conducted on tropical fish, both fresh warm water species and salt water species. Thousands of tropical fish were shipped to Philadelphia from Africa and Asia. Many had been confined to their shipping containers for over 36 hours and exhibited severe stress and damage. All tests clearly indicated that within several days, the composition containing the aloe vera extract promoted healing of damaged fish tissue and prevented infection in both fresh and salt water species of tropical fish, as well as cold water fish, such as goldfish.

The composition of Example 4, before addition to the water containing the fish, may contain about 5% to about 30% of the aloe vera gel by volume. Presently, about 10% by volume is preferred. Favorable results have been achieved with compositions containing less than 5% aloe vera gel. It is believed that a composition containing as low as 1% aloe vera gel is capable of eliciting a healing response in fish when used in the recommended dosage. If desired, other medicaments can be added to, mixed with, formed into tablets or capsules or otherwise combined with the aloe vera extract for treating various fish diseases and damaged fish tissue.

The present invention may be embodied in other specific forms without departing from the spirit or essential attributes thereof and, accordingly, reference is made to the appended claims, rather than to the foregoing specification, as indicating the scope of the invention.

I claim:

1. A process for treating damaged tissue of fish comprising topically administering to the fish an aloe vera extract selected from the group consisting of the liquid extract or gel obtained directly from the inner central zones of the leaves of the Aloe Vera plant and the gel reconstituted from powdered aloe vera extract, in an amount effective to promote healing of the damaged tissue.

2. A process according to claim 1 wherein the extract is added to water containing the fish.

3. A process according to claim 1 wherein the fish tissue has been damaged by removal of a portion of a slime coating naturally formed on fish skin and further comprising adding at least one slime-replacing compound.

4. A process according to claim 1 wherein the aloe vera extract is added to water containing the fish in an amount of about ¼ teaspoonful per 10 gallons of water.

5. A process for treating diseased or damaged tissue of fish comprising adding to water containing the fish an aqueous aloe vera gel composition comprising between about 5% and about 30% aloe vera gel by volume, up to about 7.5 g/l carboxymethyl cellulose, about 1.3 to about 25 g/l polyvinylpyrrolidone, about 12.5 to about 60 g/l sodium thiosulfate, up to about 2 g/l ethylenediaminetetraacetic acid, about 0.3 to about 1 g/l tris(hydroxymethyl)aminomethane, and about 1.3 to about 4 g/l diazolidinyl urea.

6. A process according to claim 5 wherein the carboxymethyl cellulose is present in an amount of 2.5 g/l, the polyvinylpyrrolidone is present in an amount of about 10 g/l, the sodium thiosulfate is present in an amount of about 35 g/l, the ethylenediaminetetraacetic acid is present in an amount of about 1 g/l, the tris(hydroxymethyl)aminomethane is present in an amount of about 4 g/l, and the diazolidinyl urea is present in an amount of about 2 g/l.

7. A process according to claim 6 wherein the aloe vera gel is present in the aloe vera gel composition in an amount of 10% by volume.

8. An aqueous composition for treating damaged tissue of fish in which at least a portion of a slime coating on the fish has been removed, comprising an aloe vera extract selected from the group consisting of the liquid extract or gel obtained directly from the inner central zones of the leaves of the aloe vera plant and the gel reconstituted from powdered aloe vera extract, in an amount effective to promote healing of the damaged tissue, at least one slime-replacing compound in an amount effective to promote slime replacement of at least a portion of the missing fish slime coating, a dechlorinator selected from the group consisting of sodium thiosulfate and ascorbic acid in an amount effective to neutralize the chlorine in the water, a tris(hydroxymethyl)aminomethane buffer in an amount effective to maintain the pH of the composition at least about 9.0, and a diazolidinyl urea preservative in an amount effective to prevent the inactivity of the aloe vera gel.

9. A composition according to claim 8 wherein the slime-replacing compound is selected from the group consisting of carboxymethyl cellulose in an amount of up to about 7.5 g/l, polyvinylpyrrolidone in an amount of about 1.3 to about 25 g/l, and mixtures thereof, the dechlorinator is sodium thiosulfate in an amount of about 12.5 to about 60 g/l, the tris(hydroxymethyl)aminomethane is present in an amount of about 0.3 to about 1 g/l, and the diazolidinyl urea is present in an amount of about 1.3 to about 4 g/l, the composition further comprising ethylenediaminetetraacetic acid in an amount of up to about 2 g/l.

10. A composition according to claim 9 wherein the extract is in the form of an aloe vera gel.

11. A composition according to claim 10 comprising about 10% by volume of the aloe vera gel, about 2.5 g/l carboxymethyl cellulose, about 10 g/l polyvinylpyrrolidone, about 35 g/l sodium thiosulfate, about 1 g/l ethylenediaminetetraacetic acid, about 0.4 g/l tris(hydroxymethyl)aminomethane, and about 2 g/l diazolidinyl urea.

* * * * *